United States Patent [19]

Castiglia

[11] 4,085,758
[45] Apr. 25, 1978

[54] WEIGHT-REDISTRIBUTION ORTHOPEDIC APPLIANCE

[75] Inventor: Ignatius F. Castiglia, New York, N.Y.

[73] Assignee: Lenox Hill Brace Shop, New York, N.Y.

[21] Appl. No.: 742,146

[22] Filed: Nov. 15, 1976

[51] Int. Cl.$^2$ ............................................. A61F 5/14
[52] U.S. Cl. ......................................... 128/589; 36/13
[58] Field of Search .............. 128/581, 589, 586, 607, 128/613; 36/13, 22, 25, 59, 72 A

[56] References Cited

U.S. PATENT DOCUMENTS

| 714,821 | 12/1902 | Raiser | 36/72 A |
|---|---|---|---|
| 1,317,975 | 10/1919 | Hunter | 36/13 |
| 1,972,249 | 9/1934 | Schneider | 128/589 |
| 2,047,756 | 7/1936 | Warner | 128/589 |
| 2,139,263 | 12/1938 | Fay | 128/589 |

FOREIGN PATENT DOCUMENTS

| 872,456 | 6/1942 | France | 36/13 |
|---|---|---|---|
| 742,736 | 10/1943 | Germany | 36/13 |

*Primary Examiner*—John D. Yasko
*Attorney, Agent, or Firm*—Blum, Moscovitz, Friedman & Kaplan

[57] ABSTRACT

A weight-redistribution orthopedic appliance adapted to be attached to the sole of a shoe is provided. The orthopedic appliance is a non-resilient pad that is attached to the sole of a shoe forward of the break line of the sole, the pad being sufficiently flexible to be readily contoured to the sole's surface.

12 Claims, 3 Drawing Figures

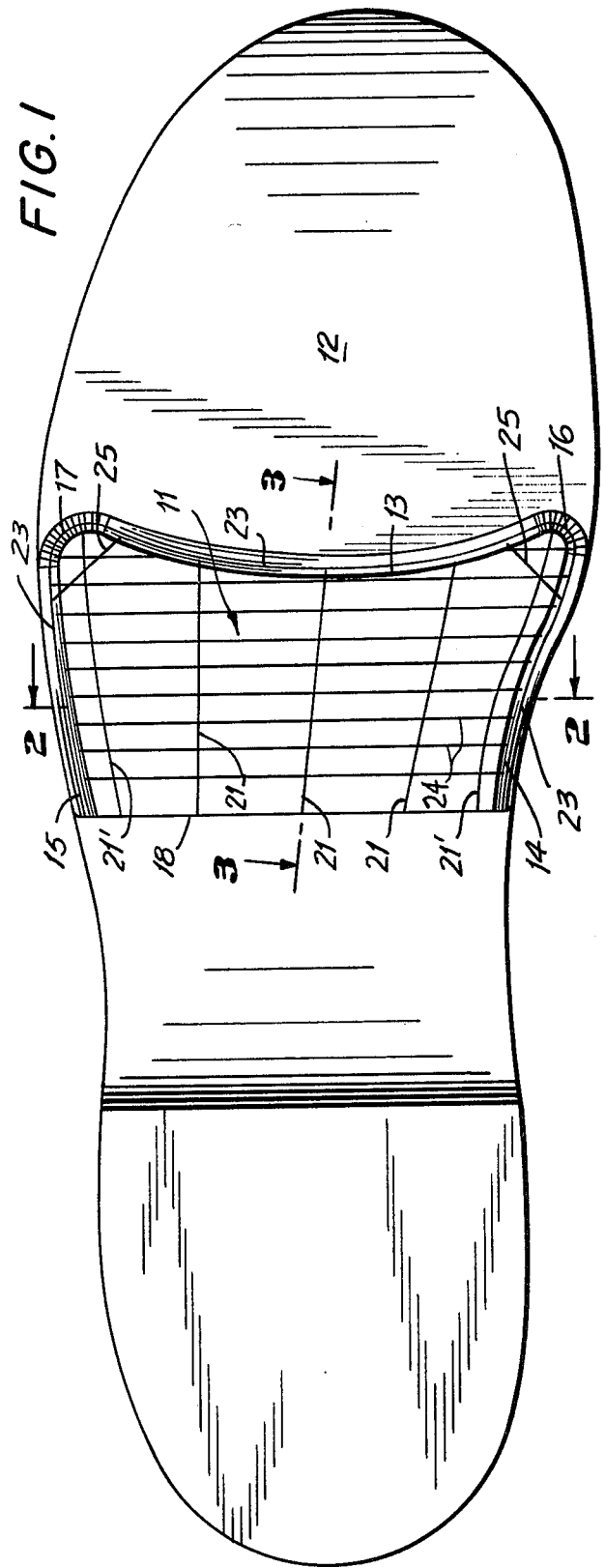
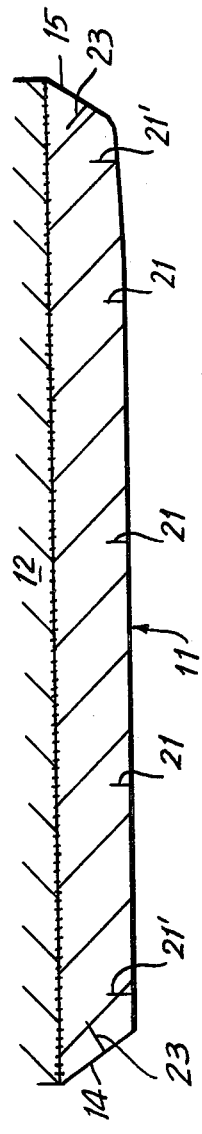
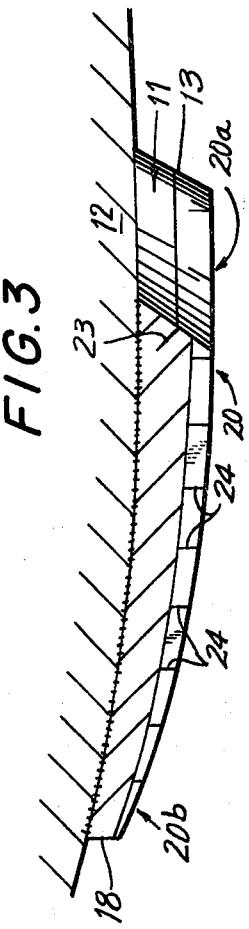

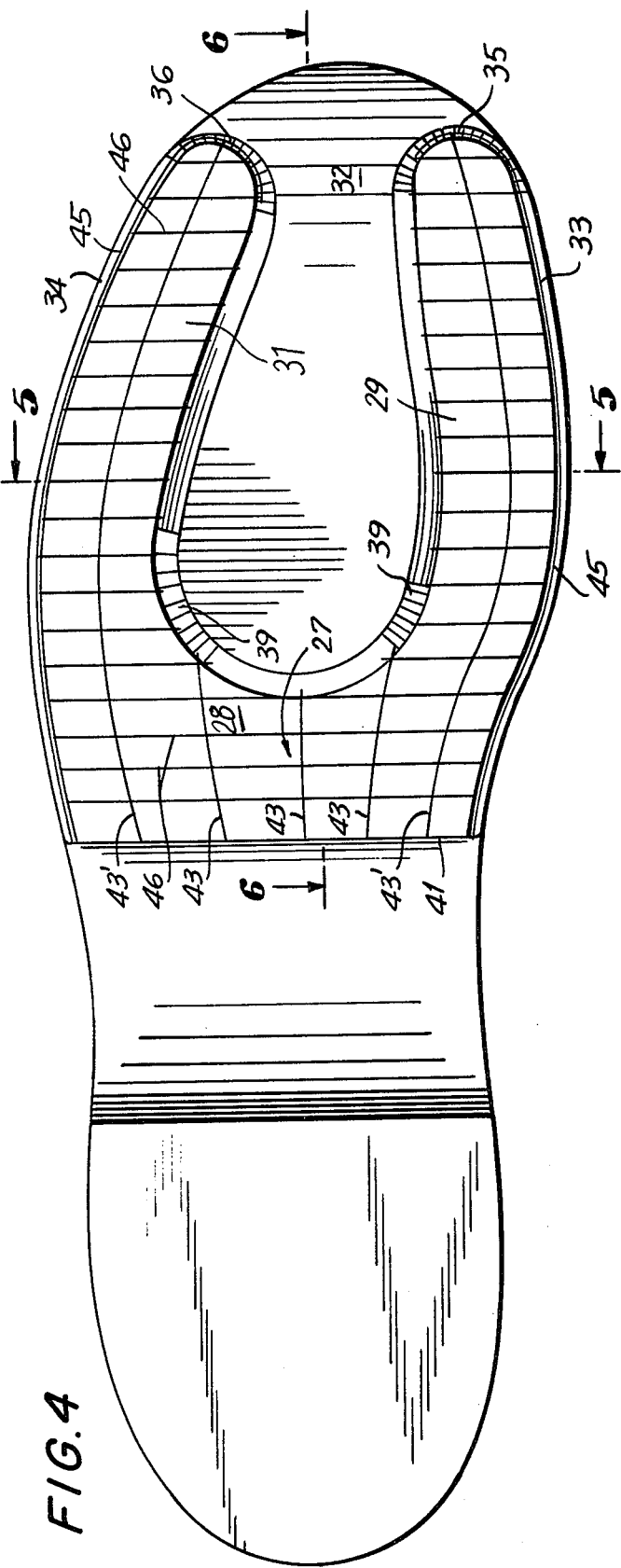
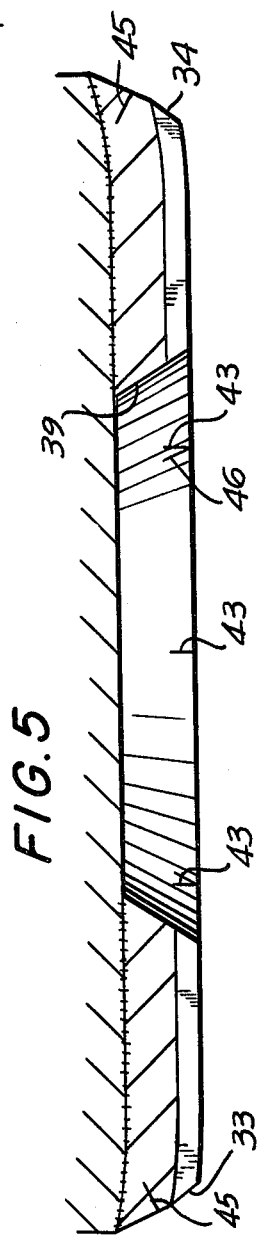
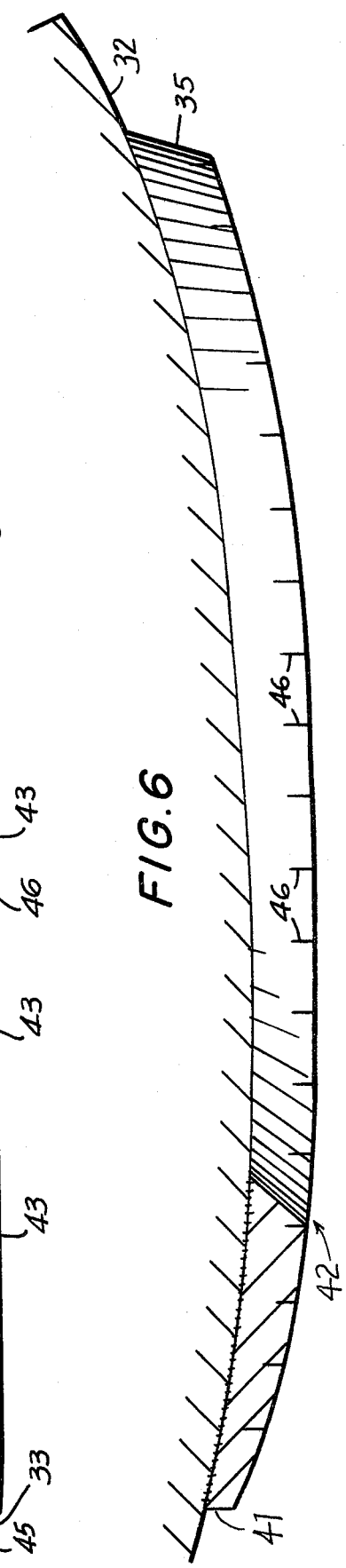

WEIGHT-REDISTRIBUTION ORTHOPEDIC APPLIANCE

BACKGROUND OF THE INVENTION

This invention relates generally to weight-redistribution orthopedic appliances, and in particular to a non-resilient pad having sufficient flexibility to permit same to be readily conformed to the sole of a shoe. While various weight-distribution orthopedic appliances, such as metatarsal pads and the like, designed for increasing the comfort of a shoe have been provided, such orthopedic appliances have been less than completely satisfactory. Specifically, when a weight-distribution pad, such as a metatarsal pad, is secured to a portion of a sole forward of the break line, the metatarsal pad must be sufficiently flexible as to permit the metatarsal pad to be conformed to the contour of the shoe in order to assure that the metatarsal pad remains rigidly secured to the sole for an extended period of time. In order to obtain such flexibility, weight-distribution pads have been formed of highly resilient materials for various reasons, one of which is to provide the necessary resiliency needed to contour the pad to the surface of the sole. Nevertheless, such resiliency permits the pad to be easily compressed during use thereby providing insufficient support for the purpose intended, to wit, weight-redistribution, and furthermore causes the pads to lose their shape over continued periods of use. Accordingly, the instant invention is directed to weight-redistribution orthopedic appliances that avoid the aforementioned problems.

SUMMARY OF THE INVENTION

Generally speaking, in accordance with the invention, weight-redistribution orthopedic appliances adapted to be attached to the sole of a shoe are provided. The appliances are constructed from a flexible, highly non-resilient material that permits the appliance to be readily attached to the underside of a sole of a shoe by means of a suitable adhesive, the flexibility permitting the appliance to be readily contoured to the contour of the sole.

In a first embodiment, the orthopedic appliance is a non-resilient flexible metatarsal pad extending from the break line of the shoe to the rear metatarsal area. In a second embodiment, the orthopedic appliance includes a pad having forward-extending arms projecting therefrom to form a generally horseshoe-like configuration.

Accordingly, it is an object of this invention to provide an improved weight-redistribution orthopedic appliance for the sole of a shoe that is easily attached thereto.

A further object of this invention is to provide a weight-redistribution orthopedic appliance for the sole of a shoe that is readily adapted to a wide variety of shoe sizes and styles.

Still a further object of this invention is to provide an improved weight-redistribution orthopedic appliance to be attached to the sole of a shoe for redistributing weight away from the metatarsal heads and/or shafts.

Still other objects and advantages of the invention will in part be obvious and will in part be apparent from the specification.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a plan view illustrating a weight-redistribution orthopedic appliance, constructed in accordance with a first embodiment of the instant invention, attached to the sole of a shoe;

FIG. 2 is a sectional view taken along line 2—2 of FIG. 1;

FIG. 3 is a sectional view taken along line 3—3 of FIG. 1;

FIG. 4 is a bottom plan view illustrating a weight-redistribution orthopedic appliance, constructed in accordance with a second embodiment of the instant invention, attached to the sole of a shoe;

FIG. 5 is a sectional view taken along line 5—5 of FIG. 4; and

FIG. 6 is a sectional view taken along line 6—6 of FIG. 4.

DETAILED DESCRIPTION OF THE PREFERRED EMBODIMENTS

Reference is now made to FIGS. 1 through 3, wherein a weight-redistribution metatarsal pad, generally indicated at 11, formed of a hard, non-resilient material such as leather, hard rubber or the like, is externally attached to the sole 12 of a shoe. The respective lengthwise sides 14 and 15 of metatarsal pad 11, when viewed with respect to the lengthwise dimension of the sole, are generally configured to follow the lengthwise peripheral edges of the sole 12, the selection of the respective side configurations depending on whether the pad is to be attached to a left shoe or a right shoe. The widthwise forward side 13 of metatarsal pad 11 is curved rearwardly along the widthwise extent of the sole and meets the lengthwise sides 14 and 15 at rounded corners 16 and 17 respectively. The thickness of the pad decreases from a thick portion, illustrated at 20a, to a thinner portion, illustrated at 20b, at the rear side 18. Accordingly, the respective lengthwise sides 14 and 25, corners 16 and 17, and forward side 13, define a continuous bevelled surface 19 that entirely frames, with the exception of the rear side 18, the metatarsal pad.

The non-resilient metatarsal pad 11 may be attached to a shoe by any suitable adhesive. Rear edge 18 of metatarsal pad 11 is attached to the sole 12 at a point proximate to the break line thereof. When metatarsal pad 11 is so attached, the pad will redistribute the wearer's weight away from the heads of the metatarsals, thus relieving pressure on the metatarsals.

As aforenoted, in a preferred embodiment the metatarsal pad is formed of leather having a thickness at the thickest portion in the range of 0.25 to 0.3125 and a thickness at the thinnest portion of the metatarsal pad in the range of 0.25 to 0.1875. In order to impart sufficient flexibility to the metatarsal pad to be contoured to the sole 12, a plurality of longitudinal slits 21 and 21' and a plurality of latitudinal slits 24 are cut into the top surface of the metatarsal pad 11. Specifically, metatarsal pad 11 includes longitudinal slits 21 which provide flexibility about the longitudinal axis of the sole 12. The outermost longitudinal slits 21' are similarly configured to the lengthwise side edges 14 and 15. The latitudinal slits 24 are disposed on the top surface of the pad 11 to provide flexibility along an axis substantially parallel to the break line of the shoe sole 12. Optionally, diagonal slits 25 located proximate to the rounded corners 16 and 17 can be utilized to provide additional flexibility. Also, a slit 23 can be cut into the continuous bevelled surface 19 at an angle of approximately 45° with respect to surface of the sole, in order to further contour the edges of the pad to the sole.

Accordingly, the longitudinal, latitudinal and diagonal slits in the top surface of the metatarsal pad provide sufficient flexibility to the metatarsal pad to permit same to bend with the shoe sole 12 when same is attached thereto. Such flexibility permits the metatarsal pad to be attachable to a wide variety of shoes without special fittings and to further permit the metatarsal pads to remain attached to the shoe during extended periods of use. Moreover, in view of the non-resilient characteristic of the material utilized to form the metatarsal pad, it is primarily through the slits that sufficient flexibility is obtained. Accordingly, the instant invention is particularly characterized by a non-resilient metatarsal pad for redistributing a person's weight away from the heads of the metatarsals which pad is constructed to permit the requisite contouring and flexibility necessary to permit the metatarsal pad to be adhesively affixed to the sole of a shoe and remain secureably fastened thereto over extended periods of time.

Reference is now made to FIGS. 4 through 6 wherein a weight-redistribution horseshoe pad, generally indicated at 27, for dealing with a further metatarsalgia condition is depicted. The horseshoe pad is formed with a rear body 28 and a pair of forward extending arms 29 and 31. The horseshoe pad includes lengthwise sides 33 and 34 respectively conforming to the lengthwise peripheral edges of the sole 32 to which the horseshoe pad is to be attached. Arms 29 and 31 terminate in rounded off end edges 35 and 36, the end edges being proximate to the toe area of the sole 32. The end edges 35 and 36 define a continuous bevelled surface with the side edges 33 and 34, respectively, and further extend on the inner peripheral sides of the arms of the horseshoe pad to define a continuous bevelled surface 39 having a steeper grade than the side and end edges. The arms 29 and 31 of the horseshoe pad 27 are of generally uniform thickness along the lengthwise and widthwise extents thereof. However, the body 28 of the metatarsal pad 27 tapers in thickness from the thickest portion proximate to the position at which the arms extend from the body, indicated at 42, rearwardly to the thinnest dimension at the rearward widthwise edge 41.

In accordance with the instant invention, horseshoe pad 27 may be constructed from leather having a thickness in the range of 0.25 to 0.3125 in the thickest portion, indicated at 42, to a thickness in the range of 0.25 to 0.1875 in the thinner portion at the rear widthwise edge 41, or any other suitable non-resilient material, and may be attached to sole 32 by any suitable adhesive. The necessary flexibility is obtained by disposing a plurality of slits in the top surface of the horseshoe pad. Specifically, a plurality of longitudinal slits 43 and 43' are disposed along the lengthwise extent of the horseshoe pad. Slits 43' are disposed along the lengthwise extent of the resepctive arms 29 and 31. A series of latitudinal slits 46 are disposed in the body and arms to provide sufficient flexibility in the lengthwise direction. Additionally, continuous slits 45 can be formed in the sides 34 and 33 at an angle of approximately 45° with respect to the surface of the sole. It is noted that the term "slits" utilized herein is used in the generic sense to refer to channels, grooves, etc., that can be found in the surfaces of the respective pads to provide the necessary flexibility. Accordingly, the horseshoe pad redistributes a person's weight away from the shafts of the metatarsals, in addition to the heads of the metatarsals, and is particularly suited to be adhesively secured to a sole of a shoe and to be readily conformed to the surface of the sole.

Accordingly, the instant invention is characterized by a weight-redistribution orthopedic applicance that is formed of a non-resilient material such as leather, hard rubber, or the like, this is provided with the flexibility necessary to permit the pad to be readily contoured to the sole of a shoe. By providing a non-resilient pad, the unwanted deforming of the orthopedic appliance inherent in resilient pads, over extended periods of use is avoided, thereby increasing the weight-redistribution function of the pad for extended periods of time, and thereby providing an easier to use, readily attachable, long lasting and improved weight-redistribution pad for treating metatarsalgia conditions.

It will thus be seen that the objects set forth above, among those made apparent from the preceding description, are efficiently attained, and since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A weight-redistribution orthopedic appliance comprising a non-resilient pad, said non-resilient pad including a securing surface adapted to be secured to the bottom of the sole of a shoe, forward of the break line of the sole said pad including an outer surface facing in substantially the same direction as the bottom of the sole of the shoe to which the securing surface is secured, and including slits selectively disposed in at least said outer surface of said pad for contouring said non-resilient pad to flexibly conform to said shoe sole, said slits being disposed in said outer surface and oriented into a first group of slits substantially parallel to a longitudinal axis of said pad and a second group of slits substantially transverse to said longitudinal slits.

2. A weight-redistribution orthopedic appliance as claimed in claim 1, wherein said non-resilient pad is leather.

3. A weight-redistribution orthopedic appliance as claimed in claim 1, wherein said non-resilient pad extends from said break line of said sole to the rearward metatarsal area of said sole and further includes a pair of forwardly extending arms, said arms extending along the periphery of said sole, forming a generally horseshoe shaped non-resilient pad.

4. A weight-redistribution orthopedic appliance as claimed in claim 3, wherein the forward ends of said arms are rounded.

5. A weight-redistribution orthopedic appliance as claimed in claim 4, wherein each said arm includes at least one slit disposed in said outer surface along the lengthwise extent thereof.

6. A weight-redistribution orthopedic appliance as claimed in claim 5, wherein said pad includes bevelled side edges along the lengthwise extent of said pad and both arms extending therefrom, said bevelled side edges including a continuous slit disposed at an angle of approximately 45° with respect to the surface of the sole.

7. A weight-redistribution orthopedic appliance as claimed in claim 1, wherein said pad extends forward to the rear metatarsal area of said sole.

8. A weight-redistribution orthopedic appliance as claimed in claim 7, wherein said pad includes a forward widthwise edge defining a continuously rearwardly receding arcuate surface.

9. A weight-redistribution orthopedic appliance as claimed in claim 8, wherein the said lengthwise side edges meet said forward widthwise edges and form forward rounded corners.

10. A weight-redistribution orthopedic appliance as claimed in claim 9, wherein at least a portion of the side and formed edges of said non-resilient pad are bevelled with respect to said top and end surfaces.

11. A weight-redistribution orthopedic appliance as claimed in claim 9, and including a continuous slit formed in said bevelled edges at an angle of approximately 45° with respect to the surface of said sole.

12. A weight-redistribution orthopedic appliance as claimed in claim 9, wherein said pad is tapered at the portion thereof disposed proximate to the rear of the break line, and gradually thickens toward the continuously receding arcuate surface.

* * * * *